United States Patent
Petenate et al.

(10) Patent No.: US 12,128,081 B2
(45) Date of Patent: Oct. 29, 2024

(54) PROCESS OF OBTAINING ENRICHED FRACTIONS OF ASSETS FROM THE ARTEMISIA GENUS, ENRICHED FRACTIONS AND BIOACTIVE COMPOSITION

(71) Applicants: UNIVERSIDADE ESTADUAL DE CAMPINAS, Campinas (BR); S DISTRIBUIDORA DE COSMETICOS, Campinas (BR)

(72) Inventors: Maria Angela De Almeida Meireles Petenate, Campinas (BR); Renata Vardanega, Campinas (BR); Gislaine Chrystina Nogueira De Faria, Campinas (BR)

(73) Assignees: UNIVERSIDADE ESTADUAL DE CAMPINAS, Campinas (BR); S DISTRIBUIDORA DE COSMETICOS, Campinas (BR)

( * ) Notice: Subject to any disclaimer, the term of this patent is extended or adjusted under 35 U.S.C. 154(b) by 458 days.

(21) Appl. No.: 17/418,640

(22) PCT Filed: Dec. 22, 2019

(86) PCT No.: PCT/BR2019/050559
§ 371 (c)(1),
(2) Date: Jun. 25, 2021

(87) PCT Pub. No.: WO2020/132730
PCT Pub. Date: Jul. 2, 2020

(65) Prior Publication Data
US 2022/0080012 A1 Mar. 17, 2022

(30) Foreign Application Priority Data
Dec. 26, 2018 (BR) ...................... 10 2018 077171-0

(51) Int. Cl.
*A61K 36/00* (2006.01)
*A61K 8/9789* (2017.01)
*A61K 36/282* (2006.01)
*A61Q 19/00* (2006.01)

(52) U.S. Cl.
CPC .......... *A61K 36/282* (2013.01); *A61K 8/9789* (2017.08); *A61Q 19/00* (2013.01); *A61K 2236/37* (2013.01); *A61K 2236/39* (2013.01); *A61K 2800/10* (2013.01)

(58) Field of Classification Search
CPC .................................................. A61K 36/282
See application file for complete search history.

(56) References Cited

PUBLICATIONS

Kohler, Extraction of artemisinin and artemisinic acid from *Artemisia annua* L. using supercritical carbon dioxide. Journal of chromatography. A, (Oct. 17, 1997) vol. 785, No. 1-2, pp. 353-360 (Year: 1997).*

* cited by examiner

*Primary Examiner* — Qiuwen Mi
(74) *Attorney, Agent, or Firm* — LUCAS & MERCANTI, LLP

(57) ABSTRACT

A process for obtaining enriched fractions of assets from the genus *Artemisia*, enriched fractions obtained by the process and bioactive composition having fraction enriched from *Artemisia*. The process uses extraction with supercritical fluid in which the differential consists of sequential extraction, in an unprecedented association of specific conditions and steps with an advantageous effect not previously found, thus obtaining enriched fractions of bioactives with different chemical compositions for a given application. The enriched fractions of assets of the genus *Artemisia* and/or its so-called bioactive compositions having fraction enriched from *Artemisia* obtained have application mainly in the pharmaceutical and cosmetic fields.

7 Claims, 4 Drawing Sheets

PROCESS OF OBTAINING ENRICHED FRACTIONS OF ASSETS FROM THE ARTEMISIA GENUS, ENRICHED FRACTIONS AND BIOACTIVE COMPOSITION

CROSS-REFERENCE TO RELATED APPLICATIONS

This application is a 371 of PCT/BR2019/050559, filed Dec. 22, 2019, which, in turn, claimed the priority of Brazilian Patent Application No. 10 2018 077171-0, filed Dec. 26, 2018, both applications are incorporated herein by reference.

TECHNICAL FIELD

The present invention describes a process for obtaining enriched fractions of active compounds from the genus *Artemisia*, preferably *Artemisia annua*, enriched fractions and the bioactive composition comprising the enriched fraction from *Artemisia*. The process uses extraction with supercritical fluid in which the differential consists of sequential extraction, in an unprecedented association of specific conditions and steps with an advantageous effect not previously found, thus obtaining enriched fractions of bioactive with different chemical compositions for a given application. The enriched fractions of bioactive of the genus *Artemisia* and/or its so-called bioactive composition comprising a fraction enriched from *Artemisia* obtained have application mainly in the pharmaceutical and cosmetic fields.

This invention belongs to the technical field of extraction and/or physical separation processes involving the use of supercritical fluid as a solvent or mobile or eluent phase.

BACKGROUND TECHNOLOGY

Extraction with supercritical fluid (SFE—Supercritical Fluid Extraction) has been used on a large scale to obtain products such as compositions based on oils and extracts from various plant matrices. The main solvent used is carbon dioxide ($CO_2$), which is an environmentally green solvent defined as GRAS (Generally Recognized As Safe), cheap and with very interesting physicochemical properties for application in extraction processes. $CO_2$ reaches a supercritical state under relatively mild temperature and pressure conditions (above 31° C. and 73.9 bar) and returns to its gaseous state under ambient conditions, allowing to obtain products completely free of solvent. In addition, small changes in the temperature and pressure conditions of the process promote important changes in the solvation capacity of supercritical $CO_2$, which, in turn, allow the extraction of compounds to be selective for certain classes of compounds. In other words, for each plant matrix used, the process is specific with conditions that allow obtaining products that can have a high added value according to the composition of bioactive substances. That is, both the product and the process must be specific for the intended applications.

*Artemisia* (*Artemisia annua*) is a plant native from Asia with aromatic leaves containing several compounds, including flavonoids, sterols, phenols, terpenes and lactones [1]. The *artemisia* essential oil has commercial interest due to the properties that the volatile *artemisia* compounds have shown: control of *Candida* ssp., combating visceral Leishmaniasis and obesity, in addition, to its potential use as an agrochemical agent due to its insecticidal action [2-5].

Artemisinin is the best-known bioactive compound of *artemisia* for being used as an Active Pharmaceutical Ingredient (IFA) in the pharmaceutical industry for the treatment of malaria caused by *Plasmodium falciparum* [6]. In 1971, artemisinin was described as a sesquiterpene lactone. Since its isolation, several artemisinin derivatives have been synthesized. In 2002, the World Health Organization (WHO) indicated the combined *artemisia* treatment as the first-line to fight malaria. In addition to its anti-malarial potential, artemisinin has also shown positive results for the treatment of blood protozoa and some types of cancer [7,8]. In addition to artemisinin, *artemisia* has other sesquiterpene lactones derived with high pharmacological activity, such as anti-inflammatory, antimicrobial and antioxidant properties.

TECHNICAL STATUS

Supercritical fluid extraction SFE) has already been used to obtain fractions enriched with bioactives of the genus *Artemisia*, in which the differential consists of at least one enriched fraction, mainly in artemisinin, aiming at the reduction of other compounds such as sesquiterpene lactone such as artemisinin and dihydroartemisinin. It is also the object of the present invention to obtain a bioactive composition comprising a fraction enriched from *Artemisia*. In 2005, Quispe-Condori et al. [9] obtained the highest yield of artemisinin (0.7%, d.b.) at 50° C. and 300 bar, and the extraction yield was 5.7%.

A study was recently carried out to optimize the extraction of artemisinin by SFE, where it was also studied the fractionation of the extract in separators [10]. These authors report that the best results were obtained when the extraction was carried out at 40° C. and 100 bar, with the first separator cooled to −7° C. In these conditions, the heavier compounds, such as waxes, were retained in the first separator, allowing obtaining an extract with 35% of active compounds in the second separator. Artemisinin was the predominant compound in the extract, but other sesquiterpene lactones such as artemisinin and dihydroartemisinin were also observed.

The following paragraphs illustrate several documents that use supercritical fluid extraction to obtain extracts containing bioactive compounds from *Artemisia*.

The documents CN103467274 and CN105237546 address the process of obtaining *Artemisia* extract containing bioactive compounds through extraction with supercritical fluid. In these documents, the pressure and temperature parameters for obtaining the extract overlap with the parameters of the present invention, differing with respect to the other characteristics of the process and the product obtained.

The document CN1304020 as well as the present invention describes some forms of extraction. According to example 4, the parameters (such as time, temperature and pressure) used in the document are within the ranges established by the present invention. In the same way as the present invention, the extraction occurs in the supercritical mode.

However, the present invention differs from this document in that it describes an extraction process with supercritical fluid in which the differential is the association of multiple stages with the process conditions, where there is variation in temperature, pressure and S/F ratio. In addition to the process being different, the present invention results in a differentiated product (highly enriched fraction) for industrial application. The process described in CN 1304020 comprises only one step, and uses an arbitrary weight ratio. The particularities of the present invention make the present proposal unprecedented and not obvious, considering that such characteristics of the process disclosed in this invention comprise at least a fraction advantageously enriched. The subject of the present invention is a bioactive composition comprising a fraction enriched from *Artemisia*.

Despite Baldino's document, L. 2018 (*ARTEMISIA ANNUA* ORGANIC SOLVENT EXTRACT, PROCESSED BY SUPERCRITICAL CO2) consider the Process of SC—$CO_2$ with the same processing parameters, proposes a strategy to concentrate artemisinin and other similar active ingredients in the final extract, which makes it different from the present invention that aims precisely to fractionate the extraction, to obtain enriched fractions of specific assets and their bioactive compositions.

Kohler's document, M. 1997 (EFFECT OF *THYMUS VULGARIS* ESSENTIAL OIL ON INTESTINAL BACTERIAL MICROBIOTA OF RAINBOW TROUT, ONCORHYNCHUS MYKISS (WALBAUM) AND BACTERIAL ISOLATES) illustrates the supercritical fluid composed of carbon dioxide and 3% methanol, with temperature and pressure set at 50° C. and 15 MPa, respectively, as addressed in the present invention. However, the differential of the present invention consists, among other characteristics such as sequential steps, it does not use methanol as cosolvent, a great advantage over Kohler's document, M. 1997.

Alberici's document, R. 2017 (AN OPTIMIZED PROCESS FOR SUPERCRITICAL CO2 EXTRACTION OF HIGH-VALUE COMPONENTS FROM *ARTEMISIA ANNUA* L FOR COSMETIC APPLICATIONS) addresses the use of a fractional extraction, using the supercritical fluid technique, for the production of essential oil, artemisinin and residual extract using fractional extraction of supercritical CO2. However, the characteristics of the process and the obtained products differ and are less advantageous compared to the present invention.

The document by Quispe Condori, Socrates. 2005 (DETERMINATION OF PROCESS PARAMETERS IN THE VARIOUS STEPS OF THE SUPERCRITICAL EXTRACTION OF NATURAL PRODUCTS: *ARTEMISIA ANNUA, CORDIA VERBENACEA, OCIMUM SELLOI* AND *FOENICULUM VULGARE*) addresses the use of a fractional extraction, using the supercritical fluid technique. Still, it should be noted that: fractional extraction is an alternative technique that allows obtaining different compounds through successive extractions by increasing the density of CO2. However, the aforementioned document does not indicate a process similar to that proposed either by sequential extraction associated with the process conditions, in addition to obtaining a differentiated product, better described below.

In addition to the works described above, there is a process for extracting and fractionating the sagebrush extract to purify the sagebrush (PI 0903275-4). In this process, the extraction is carried out preferably at 30° C. and 100 bar, and when leaving the extractor, the mixture containing the solvent (CO2) and the extract comes in contact with an adsorbent material (silica) in a fractionating column, where the artemisinin is retained. Compounds that are not retained are directed to a separator and collected in a collection bottle. Then, the fractionating column is fed with a mixture containing CO2+ethanol employing a gradient (% ethanol) from 0 to 10% to recover the artemisinin initially adsorbed on the silica column. In this process, the enriched fraction of the *artemisia* extract obtained and purified from this process showed an artemisinin content greater than 34%. The present invention differs from the previous one due to the non-use of an adsorbent column and additional steps to remove the active principle using solvents such as ethanol.

The main differential of the process of the present invention compared to the techniques commonly used in the industry is that the process is carried out sequentially using solvent considered environmentally safe under conditions of different densities, which allows obtaining enriched fractions of *Artemisia* extracts with different chemical compositions at each stage, as well as a bioactive composition comprising enriched fraction from *Artemisia*.

Considering the processes already described in the literature for obtaining and/or extracting *Artemisia* using extraction with a supercritical fluid, none of them performs the extraction sequentially, being a great differential in the association of process conditions to sequential extraction to obtain enriched fractions as shown in this invention.

SUMMARY OF THE INVENTION

It is an object of the present invention a process of obtaining enriched fractions of the genus *Artemisia* in which the differential consists of sequential extractions comprising the stages of:
  a) Extraction with $CO_2$ at a temperature of 57° C. to 65° C. and a pressure of 50 to 150 bar to obtain the enriched fraction (1);
  b) Extraction of residue material from step a) with CO2 at a temperature of 47° C. to 55° C. and a pressure of 250 to 350 bar to obtain the enriched fraction (2);
  c) Extraction of residue material from step a) with CO2 at a temperature of 47° C. to 55° C. and a pressure of 250 to 350 bar to obtain fraction (3); wherein step c) the ratio of S/F) is 5 to 7 times greater than the ratio S/F of step b).

In a preferred achievement, step a) S/F ratio is 4, step b) S/F ratio is 4.3 and step c) S/F ratio is 27.

Process in which the plant raw material belonging to the genus *Artemisia* be selected from the group comprising the species *annua, dracunculus, vulgaris, abysinica, absynthicum, aftra, cannariensis, scoparia* and combinations thereof.

In another preferred embodiment, the plant belonging to the genus *Artemisia* is *Artemisia annua*.

Process, according to any of the previous descriptions, in which step a) S/F ratio is 4, step b). S/F ratio is 4.3, and step c) S/F ratio be 27.

According to any of the descriptions prior to step a), the process is performed at a temperature of 60° C., at a pressure of 100 bar and an S/F ratio of 4.

Process, according to any of the previous descriptions, step b) be performed at a temperature of 50° C., at a pressure of 300 bar and an S/F ratio preferably of 4.3.

Process, according to any of the previous descriptions, step c) be performed at a temperature of 50° C., at a pressure of 300 bar and an S/F ratio of preferably 27.

The enriched fraction obtained by the process described above comprises high artemisinin content for application in cosmetics and pharmaceuticals.

A bioactive composition comprising an enriched fraction (2), obtained by the process described above, rich in artemisinin for application in cosmetics and pharmaceuticals.

A bioactive composition comprising an enriched fraction (1), obtained by the process described above, is rich in volatile oil and artemisinin for application in cosmetics and pharmaceuticals.

Bioactive composition because it has residual fraction (3) comprising artemisinin, deoxyartememisin and dihydroartemisin, obtained by the process described earlier for industrial application.

A bioactive composition comprising one or more fractions, obtained by the previously described process, for use in cosmetic and/or pharmaceutical formulations.

DETAILED DESCRIPTION OF THE INVENTION

For the purposes of the present invention, the raw material used to obtain enriched fractions of bioactives belongs to the genus *Artemisia* and encompasses several *Artemisia* species, including, without limiting, *annua, dracunculus, vulgaris, abysinica, absynthicum, aftra, cannariensis, scoparia* and others. Preferably the raw material is *Artemisia annua*. Any part of the plant can be used for extraction, with leaves being a preferred choice.

Extraction Process

The present invention is the process of obtaining enriched fractions of *Artemisia* with supercritical fluoride with sequential extractions, and m a preferential realization, step a) is performed at a temperature of 60° C., at a pressure of 100 bar and at an S/F ratio of 4; step b) is performed at a temperature of 50° C., at a pressure of 300 bar and at an S/F ratio of 4.3; and step c) is performed at a temperature of 50° C., a pressure of 300 bar and an S/F ratio of 27.

Figure 1:
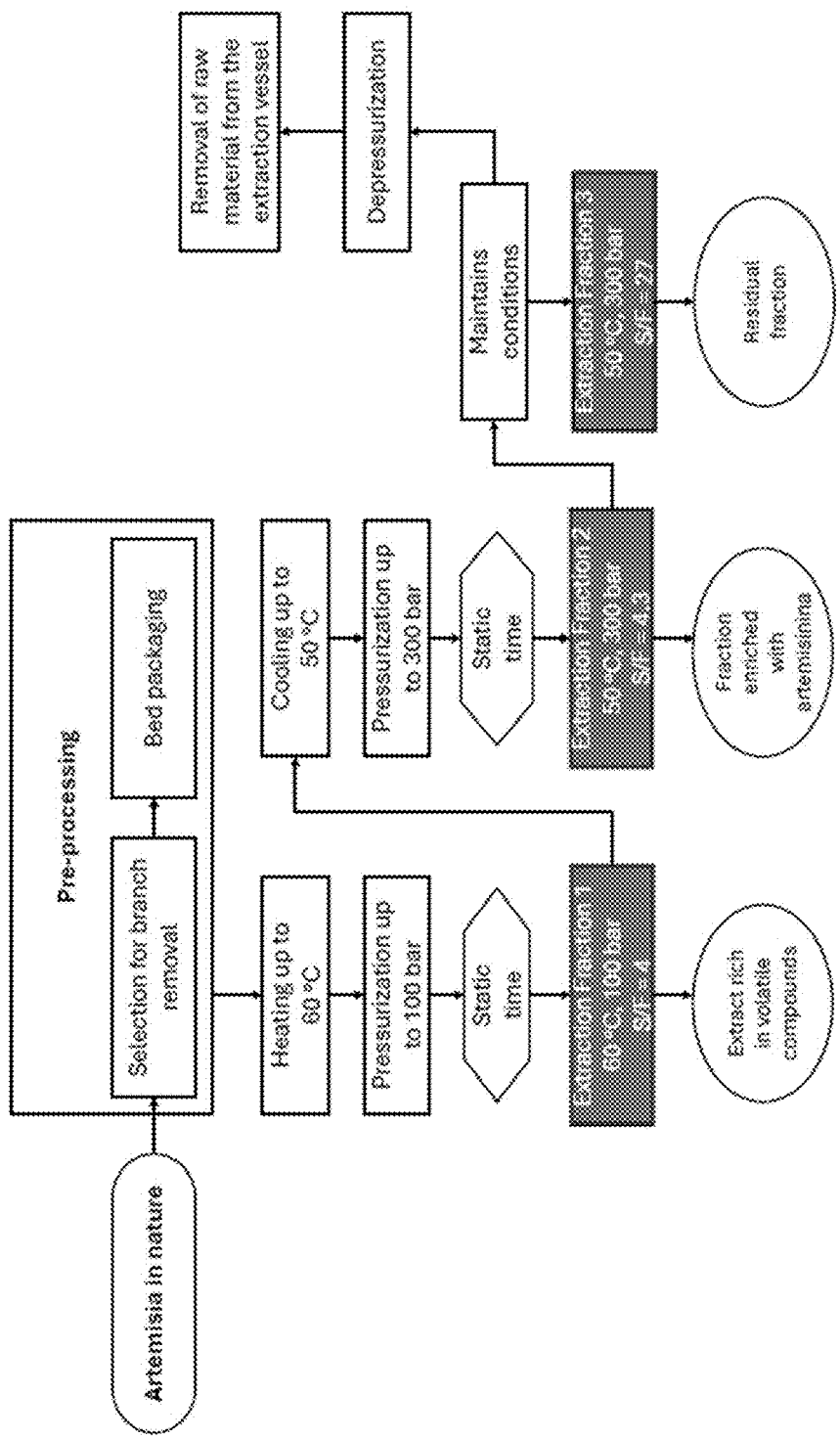
FIG. 1: Flowchart of the supercritical extraction process to obtain 3 fractions of *artemisia* extract.

The following describes the characteristics involved in each stage of the supercritical extraction process to obtain three bioactive compositions from *Artemisia* comprising the said enriched fraction (s) of *Artemisia*, each with its specific chemical composition, whose flowchart is shown in FIG. 1.

Preprocessing: The main stages of preprocessing the raw material include selecting and classifying the raw material and packaging it in the extraction vessel. The *artemisia* leaves that arrive from the field still contain small branches mixed with the leaves. Therefore, initially, *Artemisia* must go through a classification step to remove the branches because, in the preferred example, the leaves were selected as raw material to be subjected to the process of obtaining enriched fractions of bioactives of the Genus *Artemisia* of the present invention. Pre-processing can be carried out as widely as possible, not being the direct object of the present invention.

Once selected, *Artemisia* leaves are transferred to the extraction vessel or extractor to form the extraction bed itself. This step is also a 'packaging' step. The packaging step must be homogeneous to guarantee the good performance of the extraction process because the inadequate compaction of the raw material during packaging can lead to the formation of preferential paths for the flow of $CO_2$ so that the efficiency of the process is drastically reduced.

Stage 1

Bed heating: After preparing the extraction bed, heating of the extraction vessel begins so that it reaches the desired process temperature, in this case, 60° C. The form of heating may vary according to the configuration of the equipment being used, which may be through electrical resistances, a jacket with heated fluid (water or steam) or by convection (oven).

Pressurization: For the pressurization of the extraction bed, the $CO_2$ supply is opened, which is pressurized to the working pressure by means of a pump or compressor, depending on the equipment configuration. In the case of a pump, it is important to ensure that the $CO_2$ is fed into the pump in a liquid state, therefore, it must be previously cooled to a temperature around 5° C. Then, in the extraction apparatus, the $CO_2$ leaves the feed tank, passes through a coil to be cooled to −5° C. and enters the pump where it will have its pressure increased and is finally fed into the extraction vessel until it reaches the desired pressure, in this embodiment example, preferably 100 bar.

Static time: When the system reaches the desired temperature and pressure conditions, it is maintained in these conditions long enough to ensure that the system is in equilibrium. During the static time, the $CO_2$ supply is interrupted, and there is no extract output, that is, the system is maintained statically. In this example, the static time was preferably 20 min.

Enriched fraction extraction of *artemisia* assets (1): After the static time, the actual extraction period begins. During this period, the $CO_2$ flow is adjusted to the desired value and the valve of the extractor outlet is opened allowing the flow. When leaving the extractor, the mixture of $CO_2$+enriched fraction passes through an expansion valve, that is, the pressure is reduced, and a fraction enriched with bioactives of the *Artemisia* Genus is collected while the $CO_2$ separates from the enriched fraction, returning to the state gaseous for recycling, that is, when leaving the system, the $CO_2$ is condensed again and returns to the feed tank.

Step 2—Sequential Extraction (2)

Bed cooling: After the end of step 1, the bed temperature is adjusted to preferably, in this example of embodiment, 50° C., and this is maintained until the temperature stabilizes.

Pressurization: Once the previously defined temperature has been reached, pressurization is carried out to a preferential pressure of 300 bar, as described in step 1.

Static time: When the system reaches the desired temperature and pressure conditions, it is kept in these conditions for as long as necessary for the system conditions to be stabilized, in this example of implementation, preferably 20 min.

Enriched Fraction Extraction of *Artemisia* Assets (2): After reaching the temperature and pressure conditions defined for step 2, the procedure is the same as described to obtain Fraction 1.

Step 3—Sequential Extraction (3)

Enriched Fraction Extraction of *Artemisia* Assets (3): To obtain fraction 3, the extraction conditions are the same as those used in step 2, being another successive extraction with an enriched fraction (3).

Depressurization: After finishing the third step of sequential extraction, the system is depressurized by interrupting the $CO_2$ feed and relieving the pressure in the extraction vessel.

Removal of the extraction bed: Once the system is completely depressurized, raw material is removed from the extraction vessel so that new raw material is fed and begins a new cycle.

EXAMPLES OF IMPLEMENTATION

Example 1—Process of Obtaining Enriched Fractions of Bioactives of the Genus *Artemisia*, Enriched Fractions and Bioactive Composition Comprising Said Fractions Enriched from *Artemisia*

The fractions enriched to be incorporated into the bioactive composition and/or cosmetic formulation to be submitted to efficacy and safety tests were obtained by the process performed in a pilot extraction unit (Thar Technologies, Pittsburgh, USA) equipped with 2 extraction vessels of 5 L. In this case, 1400 g of raw material were used. The CO2 flow rate used was 140 g/min in all stages, whose conditions used are presented in Table 1. The enriched fractions were collected in the separators after the end of each sequential extraction stage, and the operating conditions of the separators are also presented in Table 1. The separation conditions were maintained for all sequential extraction steps. This example served as a demonstration of the realization of the present invention, so that the conditions, sequences and scale-up parameters are properly described in the claims and throughout the descriptive report successfully. Enriched fractions have been incorporated into bioactive compositions and/or product formulations for testing.

TABLE 1

Process conditions used on a pilot scale (5 L vessels) to obtain the three enriched fractions of bioactives of genus *Artemisia*.

| | | Extraction | | | |
|---|---|---|---|---|---|
| Step | Temperature (° C.) | Pressure (bar) | S/F | Flow (g CO2/min) | Time (min) |
| 1 | 60 | 100 | 4.0 | 140 | 50 |
| 2 | 50 | 300 | 4.3 | 140 | 55 |
| 3 | 50 | 300 | 27 | 140 | 273 |

| | Separation | |
|---|---|---|
| Separator | Temperature (° C.) | Pressure (bar) |
| 1 | 40 | 80 |
| 2 | 35 | 75 |
| 3 | 40 | 60 |

Figure 2:
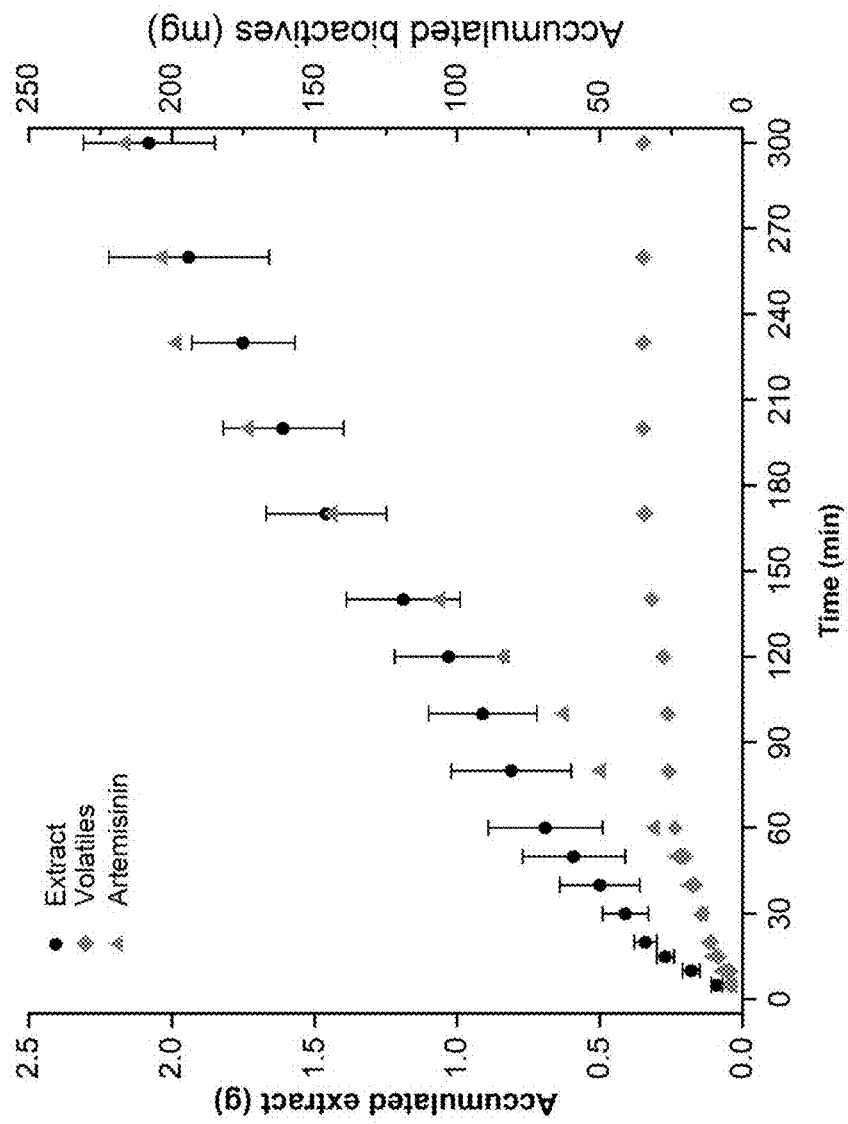
FIG. 2: Enriched fraction extraction curve of *artemisia* obtained by SFE at 60° C. and 100 bar (Step 1).

Example 2—Kinetic Study to Obtain Fraction 1—Enriched Fraction Comprising Mostly Volatile Oil The first global extraction curve was constructed by preferably employing a condition of 60° C. and 100 bar, which corresponds to the first stage of the sequential extraction process that aims to obtain an enriched fraction comprising as much volatile oil as possible with the lowest possible artemisinin presence. FIG. 2 shows that the enriched fraction mass accumulated over time had an increasing behavior during the 300 minutes of extraction, while the accumulation of volatile compounds in the fraction was significant until the first 50 minutes of extraction, and after this time, the increase in the amount of volatiles was derisory. Artemisinin in the fraction presented a differentiated behavior over time. Until the first 50 minutes, the extracted artemisinin mass present in fraction 1 was similar to the volatile compound mass obtained, and, from this time on, a significant increase in the extracted artemisinin mass (another fraction) is observed. This behavior suggests that at the beginning of the process, the solubilization of volatiles prevailed and, once these compounds were exhausted, artemisinin began to be extracted at a higher rate. In view of this result, it is observed that the first stage of the extraction process, preferably 50 minutes of process at 60° C. and 100 bar, it was possible to recover practically all the volatile oil of *Artemisia* in the enriched fraction 1 with the smallest possible amount of artemisinin. In 50 minutes of process, S/F was 4, and the extraction yield was 1.0%, resulting in an enriched fraction comprising volatile oil from *Artemisia* with 35 mg/g of volatile compounds and 39 mg/g of artemisinin. It is noted that although the extract presents a quantity of volatile compounds and similar artemisinin, artemisinin extracted up to 50 min of process represents only, in this example, 10.7% of the total artemisinin extracted over the 300 min of process.

Example 3—Kinetic Study to Obtain the Residual Fraction

Figure 3:
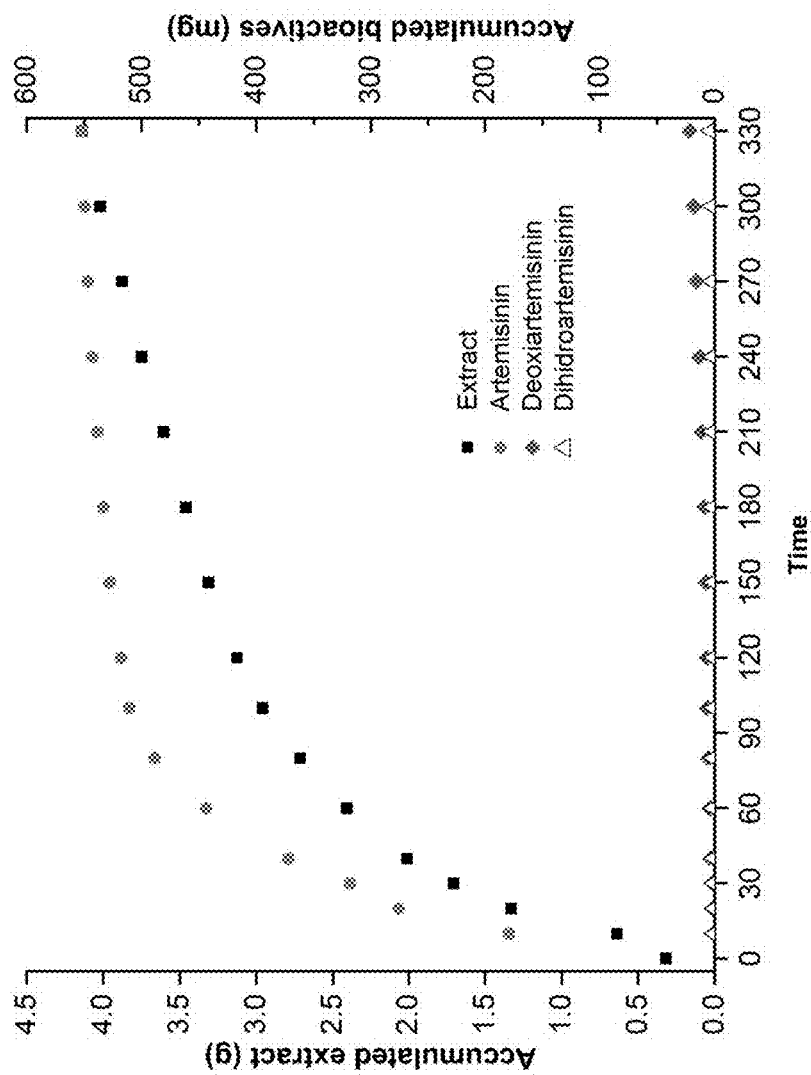
FIG. 3: Enriched fraction extraction curve of *Artemisia* obtained by SFE at 50° C. and 300 bar.
Figure 4:
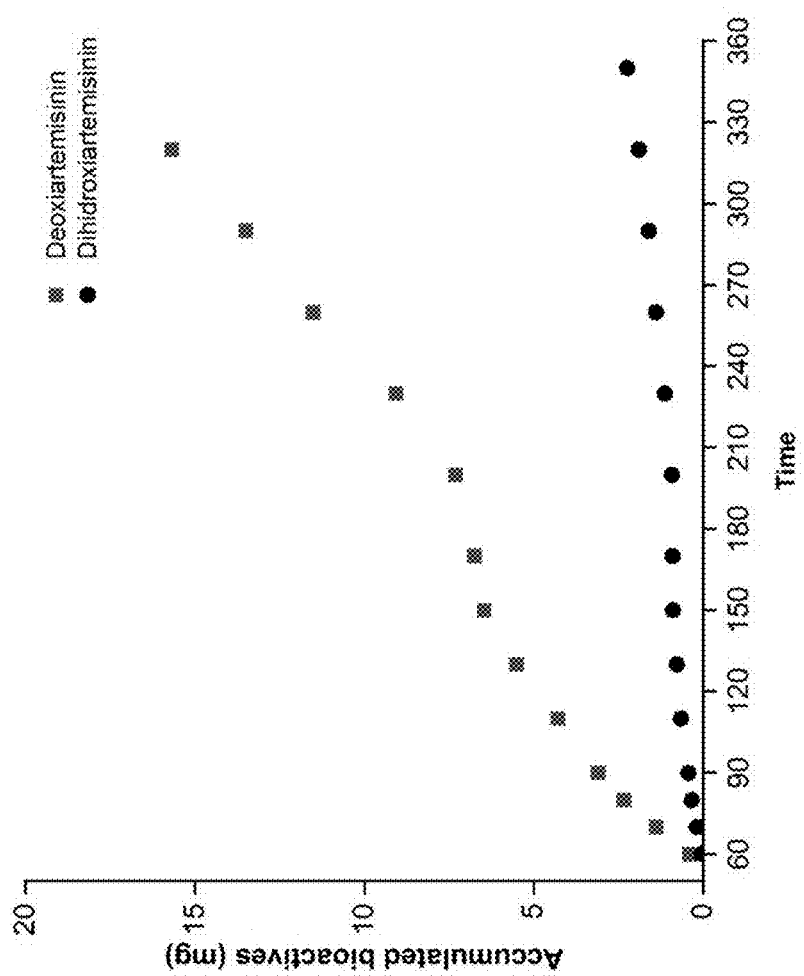
FIG. 4: Increase of the curves of enriched fractions comprising deoxyartemisinin and dihydroartemisinin.

To remove most of the artemisinin from the raw material, the present invention describes step 2 (second sequential supercritical extraction) as being the step to obtain the fraction enriched with artemisinin both concerning its content with respect to the other bioactive substances analyzed in relation to the higher mass yield of artemisinin capable of being extracted from the raw material, and step 3 obtained a fraction considered residual, that is, it had a residual artemisinin content similar to that observed in "E4", being E4 obtained by a conventional extraction process. For this, in this example of implementation, step 1 obtained a fraction enriched (1) in volatile oil as previously optimized, that is, using 60° C. and 100 bar and S/F=4 and, then, a sequential extraction (2) with the extraction conditions preferably 50° C./300 bar. Therefore, a kinetic curve was performed under these conditions and is shown in FIG. 3.

In this case, it was possible to observe that artemisinin was preferably extracted at the beginning of the process, since after 150 min. practically the entire mass of artemisinin was recovered. Deoxyartemisinin, on the other, showed a different behavior. After 150 min of process, its extraction rate was increased, suggesting that deoxyartemisinin is extracted after the depletion of artemisinin from the plant (FIG. 3 b). In this way, the extraction process can be carried out in the second way: Step 1 to 60° C./100 bar and S/F=4 for recovery of volatile oil corresponding to fraction1; Step 2 at 50° C./300 bar and S/F=4.3 for recovery of the fraction rich in artemisinin (Fraction 2) and Step 3 at 50° C./300 bar and S/F=27 for recovery of fraction 3 that corresponds to the residual fraction with a chemical composition similar to that observed in the E4 sample.

Therefore, the production of 5 g of the extract corresponding to Fraction 3 was used in biological tests of efficacy and safety. The characterization of this extract is shown in Table 3, where it is possible to observe that this time the residual extract (Fraction 3) presented an artemisinin content similar to that obtained in sample E4. Also, it is important to mention that Fraction 1, which is enriched in volatile compounds, also has an expressive artemisinin content, which is due to the fact that this compound has high CO2 solubility. To reduce the artemisinin content of this fraction, it would be necessary to use other separation techniques, such as adsorption, precipitation, among others.

TABLE 3

Results of the process of obtaining fractions enriched from *Artemisia*, with sequential extraction, carried out for the production of 5 g of extract for testing.

| Fraction | Yield (%) | Artemisinin TLC (%) | Artemisinina LC-MS (%) | Deoxiartemisinina (%) | Dihydroartemisinin (%) |
|---|---|---|---|---|---|
| 1 | 0.4 ± 0.1 | 31 ± 5 | 40.3 ± 0.2 | 1.8 ± 0.2 | 0.0100 ± 0.0002 |
| 2 | 2.2 ± 0.2 | 27 ± 5 | 33.1 ± 0.2 | 1.45 ± 0.05 | 0.0060 ± 0.0005 |
| 3 | 1.8 ± 0.3 | 12.8 ± 0.8 | 8.2 ± 0.1 | 0.44 ± 0.01 | <LQ |
| E4 | — | 8.3 ± 0.2 | 8.5 ± 0.1 | 0.71 ± 0.01 | 0.005 ± 0.001 |

*Result calculated as the ± standard deviation of four extraction processes. To obtain 5 g of Fraction 3 (equivalent to E4) it was necessary to perform the process 4 times, employing 65 g of raw material each time (260 g in total)

Example 4—Scale-Up

For the scale-up study, two criteria were evaluated: 1) S/F; t constants and 2) S/F; Constant flow. The results of extraction yield are presented in Table 4, where it is observed that the S/F criterion; t constant provided more similar data with those obtained in the 300 mL scale. Therefore, this was the criterion used to increase the scale of the process.

TABLE 4

Yield of the processes of obtaining fractions enriched from *Artemisia* with sequential extractions performed with different scale increase criteria obtained in a 1 L vessel

| c | Process condition | Yield (%) S/F; t constant | Yield (%) S/F; flow rate |
|---|---|---|---|
| 1 | 60° C./100 bar S/F = 4 | 0.46 | 0.33 |
| 2 | 50° C./300 bar S/F = 4.3 | 2.16 | 2.41 |
| 3 | 50° C./300 bar S/F = 27 | 1.99 | 1.43 |

With the scale-up criterion defined, extractions were then performed in a 1 L scale vessel, the data of which are shown in Table 5. It is possible to observe that the yield of step 1 obtained on the 1 L scale was significantly lower than that obtained on the smaller scale, while the performance of the other stages was similar. On the other hand, the artemisinin content obtained on the 1 L scale was similar to that obtained on the smaller scale for fractions and 2. At the same time, step 3 presented a higher artemisinin content on the scale increase. However, the scaling up presented satisfactory performance, and it was possible to proceed to the production stage of enriched fractions and, consequently, bioactive compositions on a pilot scale using the same scaling-up criteria.

TABLE 5

Comparison between the results obtained in the vessels of 300 mL and 1 L

| Fraction | Yield (%) | | Artemisinin content (%) | |
|---|---|---|---|---|
| Scale | 300 mL | 1 L | 300 mL | 1 L |
| 1 | 0.4 ± 0.1 | 0.14 ± 0.02 | 31 ± 5 | 32 ± 5 |
| 2 | 2.2 ± 0.2 | 2.3 ± 0.2 | 27 ± 5 | 22 ± 3 |
| 3 | 1.8 ± 0.3 | 1.7 ± 0.2 | 12.8 ± 0.8 | 20 ± 3 |

Example 5—Production of Enriched Fractions and/or Bioactive Compositions

The last stage of the project comprised the production of fractions on a pilot scale to obtain the amount necessary to be incorporated into bioactive compositions and/or cosmetic formulation submitted to efficacy and safety tests. The process conditions used are shown in Table 1 and the results obtained are presented in Table 6. Table 6 also presents the results of the obtained fractions on the 300 mL scale and the data from the E4 sample to facilitate the comparison of process performance. The process carried out in the pilot unit presented fractions with yield and composition quite similar to that obtained in the smaller scale and also with the E4 sample, which is the sample obtained by conventional process and which was intended to reproduce through extraction with supercritical fluid.

TABLE 6

Comparison between the results obtained on a pilot scale, on the 300 mL scale and the data of the E4 sample

| Fraction | Yield (%) | Artemisinin (%) | Deoxi-artemisinin (%) | Dihydroartemisinin (%) |
|---|---|---|---|---|
| Piloto Scale | | | | |
| 1 | 0.4 ± 0.1 | 39 ± 3 | 2.3 ± 0.1 | 0.006 ± 0.001 |
| 2 | 1.56 ± 0.02 | 22 ± 3 | 1.4 ± 0.1 | 0.001 |
| 3 | 2.04 ± 0.03 | 9 ± 1 | 0.69 ± 0.04 | <LQ |
| Scale 300 mL | | | | |
| 1 | 0.4 ± 0.1 | 40.3 ± 0.2 | 1.8 ± 0.2 | 0.0100 ± 0.0002 |
| 2 | 2.2 ± 0.2 | 33.1 ± 0.2 | 1.45 + 0.05 | 0.0060 ± 0.0005 |
| 3 | 1.8 ± 0.3 | 8.2 ± 0.1 | 0.44 ± 0.01 | <LQ |
| E4 | | 8.5 ± 0.1 | 0.71 ± 0.01 | 0.005 ± 0.001 |

The present patent allowed to describe a process of obtaining enriched fractions from *Artemisia* with sequential extractions with supercritical fluid to obtain 3 fractions of *Artemisia* bioactive, being a fraction rich in volatile compounds (Fraction 1), a rich fraction in artemisinin (Fraction 2) and the residual fraction (Fraction 3) with a composition similar to the sample E4 obtained by conventional process and which presented positive results in preliminary tests of anti-inflammatory action.
1. Objects of the present invention are a process for obtaining enriched fractions of assets of the genus *Artemisia*, as previously described, fractions enriched from *Artemisia* and bioactive composition comprising fraction enriched from *Artemisia*.

BIBLIOGRAPHY

[1] A. Sadiq, M. Q. Hayat, M. Ashraf, Ethnopharmacology of *Artemisia annua* L.: A Review, in: T. Aftab, J. F. S.

Ferreira, M. M. A. Khan, M. Naeem (Eds.) *Artemisia annua*—Pharmacology and Biotechnology, Springer Berlin Heidelberg, Berlin, Heidelberg, 2014, pp. 9-25.

[2] F. Santomauro, R. Donato, C. Sacco, G. Pini, G. Flamini, A. R. Bilia, Vapour and liquid-phase *Artemisia annua* essential oil activities against several clinical strains of *Candida*, (2016).

[3] M. Islamuddin, G. Chouhan, M. Y. Want, M. Tyagi, M. Z. Abdin, D. Sahal, F. Afrin, Leishmanicidal activities of *Artemisia annua* leaf essential oil against visceral leishmaniasis, Frontiers in microbiology, 5 (2014) 626.

[4] E. C. Magiero, J. Assmann, J. Marchese, D. Capelin, M. Paladini, M. Trezzi, Efeito alelopático de *Artemisia annua* L. na germinação e desenvolvimento inicial de plântulas de alface (*Lactuca sativa* L.) e leiteiro (*Euphorbia heterophylla* L.), Revista Brasileira de Plantas Medicinais, 11 (2009) 317-324.

[5] C. Morvillo, E. de la Fuente, A. Gil, M. Martinez-Ghersa, J. L. González-Andújar, Competitive and allelopathic interference between soybean crop and annual wormwood (*Artemisia annua* L.) under field conditions, European Journal of Agronomy, 34 (2011) 211-221.

[6] M. Enserink, Source of new hope against malaria is in short supply: new drugs based on an old Chinese cure could save countless lives in Africa, if health agencies and companies can find ways to make enough, Science, 307 (2005) 33-34.

[7] D. Chaturvedi, A. Goswami, P. P. Saikia, N. C. Barua, P. G. Rao, Artemisinin and its derivatives: a novel class of anti-malarial and anti-cancer agents, Chemical Society Reviews, 39 (2010) 435-454.

[8] T. Efferth, Molecular pharmacology and pharmacogenomics of artemisinin and its derivatives in cancer cells, Current drug targets, 7 (2006) 407-421.

[9] S. Quispe-Condori, Global yield isotherms and kinetic of artemisinin extraction from *Artemisia annua* L leaves using supercritical carbon dioxide, The Journal of Supercritical Fluids, 36 (2005) 40-48.

[10] L. Baldino, E. Reverchon, G. Della Porta, An optimized process for SC—CO2 extraction of antimalarial compounds from *Artemisia annua* L, The Journal of Supercritical Fluids, 128 (2017) 89-93.

What is claimed is:

1. A process of obtaining a fraction enriched from the Genus *Artemisia* comprising sequential extractions comprising the stages of:
    a) conducting a CO2 extraction at a temperature of 57° C. to 65° C. and a pressure of 50 to 150 bar to obtain a first enriched fraction;
    b) conducting sequential extraction of a residue of the first enriched fraction obtained from step a) with CO2 at a temperature of 47° C. to 55° C. and a pressure of 250 to 350 bar to obtain a second enriched fraction; and
    c) conducting sequential extraction of a residue obtained from step b) with CO2 at a temperature of 47° C. to 55° C. and a pressure of 250 to 350 bar to obtain a residual fraction wherein a S/F (solvent to feed) ratio of step c) is 5 to 7 times greater than the S/F ratio of step b).

2. The process according to claim 1, wherein a plant raw material belonging to the genus *Artemisia* is selected from the group consisting of the species *annua, dracunculus, vulgaris, abysinica, absynthicum, aftra, cannariensis, scoparia* and combinations thereof.

3. The process according to claim 2, wherein the raw material is *Artemisia annua*.

4. The process according to claim 1, wherein in step a) the S/F ratio is 4, in step b) the S/F ratio is 4.3 and in step c) the S/F ratio is 27.

5. The process according to claim 1, wherein step a) is carried out at the temperature of 60° C., the pressure of 100 bar and the S/F ratio of 4.

6. The process according to claim 1, wherein step b) is carried out at the temperature of 50° C., the pressure of 300 bar and the S/F ratio of 4.3.

7. The process according to claim 1 wherein step c) is carried out at the temperature of 50° C., the pressure of 300 bar and the S/F ratio of 27.

* * * * *